United States Patent [19]

Horn

[11] Patent Number: 4,718,075
[45] Date of Patent: Jan. 5, 1988

[54] RASTER SCAN ANODE X-RAY TUBE

[75] Inventor: Michael Horn, Selden, N.Y.

[73] Assignee: Grumman Aerospace Corporation, Bethpage, N.Y.

[21] Appl. No.: 845,642

[22] Filed: Mar. 28, 1986

[51] Int. Cl.⁴ .............................................. H05G 1/08
[52] U.S. Cl. .................................... 378/91; 378/99; 378/137; 250/370; 358/111
[58] Field of Search ................. 378/12, 19, 93–94, 378/99, 145–146, 113, 137, 91; 358/111; 250/370 G

[56] References Cited

U.S. PATENT DOCUMENTS

| | | | |
|---|---|---|---|
| 2,153,586 | 4/1939 | Nicolson | 178/7.5 |
| 2,638,554 | 5/1953 | Bartow et al. | 250/99 |
| 2,667,585 | 1/1954 | Gradstein | 250/61.5 |
| 2,730,566 | 1/1956 | Bartow et al. | 178/6.5 |
| 3,101,407 | 8/1963 | Shipman, Jr. | 250/71.5 |
| 3,176,137 | 3/1965 | Hoffmann | 250/99 |
| 3,622,785 | 11/1971 | Irwin et al. | 250/77 |
| 3,665,184 | 5/1972 | Schagen | 250/60 |
| 3,833,810 | 9/1974 | Efanov et al. | 250/273 |
| 3,949,229 | 4/1976 | Albert | 378/99 |
| 4,032,787 | 6/1977 | Albert | 378/99 |
| 4,147,935 | 4/1979 | Warrikhoff | 378/99 |
| 4,179,100 | 12/1979 | Sashin et al. | 250/416 |
| 4,250,425 | 2/1981 | Gabbey et al. | 313/60 |
| 4,352,986 | 10/1982 | Pfeiler | 378/14 |
| 4,398,302 | 8/1983 | Pfeiler | 378/146 |
| 4,442,539 | 4/1984 | Aichinger et al. | 378/207 |

FOREIGN PATENT DOCUMENTS

| | | | |
|---|---|---|---|
| 0064894 | 5/1977 | Japan | 378/19 |
| 0132985 | 11/1978 | Japan | 378/19 |
| 0018293 | 2/1979 | Japan | 378/12 |

Primary Examiner—Craig E. Church
Assistant Examiner—John C. Freeman
Attorney, Agent, or Firm—Stetina and Brunda

[57] ABSTRACT

An apparatus and method are provided for X-ray imagery of an object comprising an X-ray source adapted to variably dispose of a point source of X-rays about a first surface of the X-ray source and a detector adapted to receive the X-rays and translate the X-rays into electrical signals. The detector is adapted to selectively respond to incident X-rays, e.g., in accordance with the angle of incidence of the X-rays upon the surface of the detector. The detector may be formed of an array of individual detector elements, or may comprise a light transducer disposed adjacent the input to a television camera. The interrogation of the detector elements, or scan of the television camera image, may be synchronized with the movement of the X-ray source such that the spacial relationship between the movement of the point source and the sampled detector element, or scan point of the television camera, remain substantially constant as the point source moves.

28 Claims, 5 Drawing Figures

RASTER SCAN ANODE X-RAY TUBE

BACKGROUND OF THE INVENTION

The present invention relates to X-ray imaging devices. More particularly, the invention relates to devices for selectively imaging objects by limiting detector responses to variably selected portions of the X-ray beam.

X-rays are shortwave electromagnetic vibrations which can penetrate solid matter. They are produced when, in a vacuum, electrons are released, accelerated and then abruptly retarded. To release electrons, the tungsten filament in an X-ray tube is heated to incandescence (white heat) by passing an electric current through it. The electrons are accelerated by a high voltage (ranging from about ten thousand to some hundreds of thousands of volts) between the anode (positive) and the cathode (negative) and impinge on the anode. When the stream of very fast high-energy electrons strikes a metallic anode, the electrons are rapidly slowed down, and some of them penetrate into the metal. High energy electrons that penetrate into the metal atom may dislodge one or more inner electrons of that atom. The vacant place is then taken by one of the outer electrons which thus leap from the outer to an inner "shell" and, in so doing, emit energy in the form of radiation, i.e., X-rays.

In some contemporary X-rays tubes, the anode, usually referred to as the "target", is of the rotating disk type, so that the electron beam is constantly striking a different point of the anode perimeter. The X-ray tube itself is made of glass, but enclosed in a protected casing that may be filled with oil to absorb the heat produced. The high voltage for operating the tube is supplied by a transformer with the alternating current rectified by means of rectifier tubes, or by means of barrier-layer rectifiers.

Because of their short wavelength ($10^{-8}$ to $10^{-10}$ cm) X-rays can pass through objects that are opaque to ordinary light, and form shadow images of those objects on a film or fluorescent screen. Aside from the well recognized medical application of X-ray devices, they are also used to determine the mechanical integrity of structures that cannot readily be examined, such as structural members within an aircraft, or the like. In those applications X-ray devices permit the user to make an onsight inspection of, for example, a hidden structural joint, without having to remove the aircraft to a maintenance facility and disassemble outer surface members.

In order to take fullest advantage of the use of X-ray devices to perform structural examinations in field use, it is necessary that the device be readily portable and require a minimum of precise alignment before useful results can be obtained. Many contemporary X-ray devices require a fixed relation between the X-ray source and the X-ray detector, and are therefore unsuitable for many field uses. The present invention is directed to a device wherein the X-ray source and X-ray detector may be independently moved, and the device satisfactorily operated to produce X-ray imagery of an object through selective synchronization of the X-ray generating and X-ray detecting functions.

In most instances, X-rays are imaged on a film consisting of an acetate cellulose base coated with an emulsion of silver halide and gelatin. Alternatively, "live" X-ray images may be created on a fluorescent screen coated with barium platinocyanide. In yet another construction, X-ray images may be focused on a detector or array matrix formed of individual detector elements that generate an electrical voltage or current proportional to the intensity of the incident X-rays. Such a detector matrix may be scanned, or "interrogated" at a very high rate in order to produce a pattern or electrical signals representative of the X-ray pattern incident upon the matrix. That pattern may then be communicated to a monitor such as a television screen where it is illustrated for viewing.

X-ray sources typically generate X-rays in a fan-like pattern from a point source. When the point source is moved about in a pattern, each point in the pattern generates a separate fan-like pattern of X-rays. As a consequence of the movement of the X-ray point source, the X-ray beams pass through the object being X-rayed at differing angles and form shadows as ther paths overlap on route to the photographic or detection surface. The resulting images may, therefore, exhibit a lack of sharpness and uniformity. Various devices have been utilized to collimate the X-rays emitted from the point source, or otherwise enhance the sharpness of the image. Those devices include diaphragms that have narrow slits or appertures, as well as other selectively transmissive members that are disposed in front of the point source so as to restrict passage of oblique X-ray beams. Such devices typically require precise placement with respect to the point source of X-rays and the detection surface. Consequently, those devices are inadequate for many field uses in that they lack the flexibility to vary the angle at which the incident X-rays may be directed and observed in order to get a clearer picture of an irregular shaped object.

The present invention is directed to addressing those and other deficiencies in providing an X-ray imaging system that is portable and is adapted to readily permit selective imaging of X-rays impinging the detector surface from different angles so as to enhance the image quality, and reduce shadows generated by the interaction of overlapping X-ray beams.

SUMMARY OF THE INVENTION

An apparatus and method are disclosed for X-ray imagery of an object. The invention permits selective X-ray imagery of the object from different angles to reduce shadows generated by the interaction of overlapping X-ray beam paths. The present invention comprises an X-ray source adapted to variably dispose of a point source of X-rays about a first surface of the X-ray source and a detector adapted to receive the X-rays and translate the X-rays into electrical signals. The detector is adapted to selectively respond to incident X-rays, e.g., in accordance with the angle of incidence of the X-rays upon the surface of the detector. The detector may be formed of an array of individual detector elements, or may comprise a light trnsducer operatively coupled to the input to a television camera. The interrogation of the detector elements, or scan of the television camera image is synchronized with the movement of the X-ray source such that the spatial relationship between the movement of the point source and the sampled detector element, or scan point of the television camera, remain substantially constant as the point source moves.

The synchronization may be varied to permit normal or oblique angle views of the object to be imaged. Each view may be stored and subsequently processed to provide three dimensional imagery of the object.

BRIEF DESCRIPTION OF THE DRAWINGS

FIG. 5 is a circuit diagram illustrating use of the invention with a television camera.

DETAILED DESCRIPTION OF THE PREFERRED EMBODIMENT

Figures 1, 2:
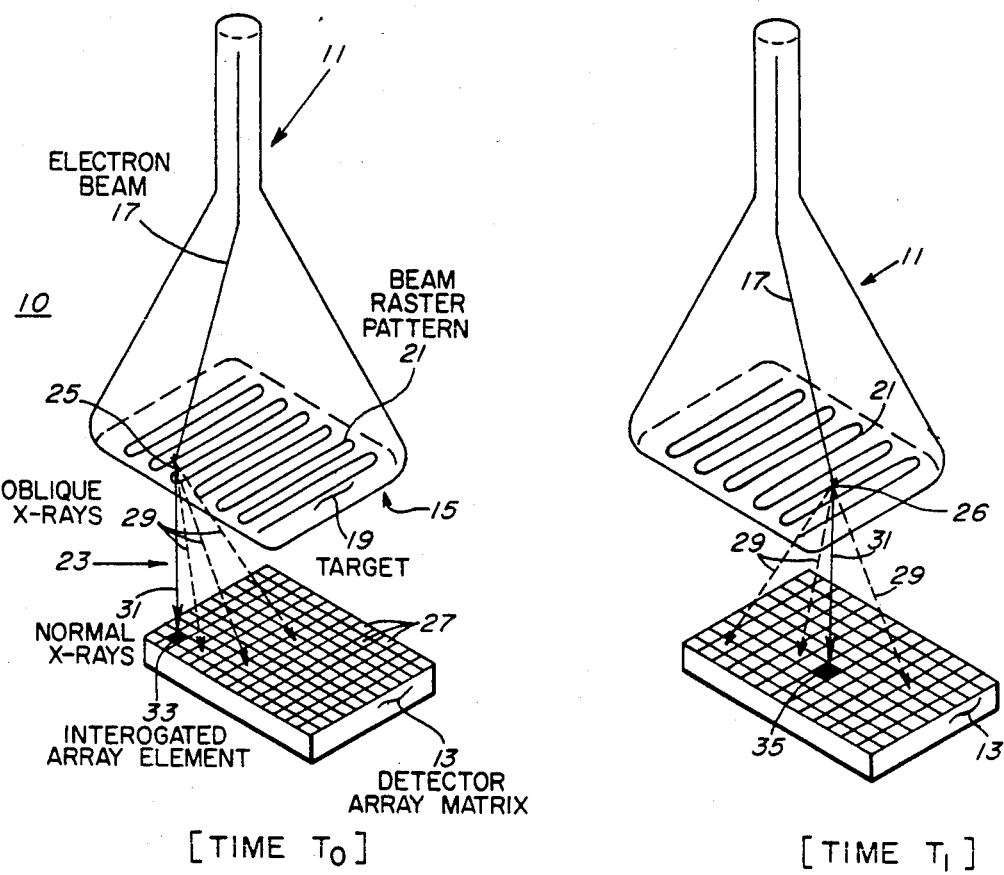
FIGS. 1 and 2 are perspective views of an X-ray imaging device in accordance with the present invention illustrating the relation between the point source and the incident X-rays, and the point source at times $T_0$ and $T_1$.

Referring to FIG. 1, X-ray imaging apparatus at 10 is illustrated therein. The apparatus includes an X-ray tube 11 and detector 13, preferably formed as an array matrix of detector elements 27. X-ray tube 11 may be any of a number of commercially available X-ray tubes adapted to generate X-ray beams from variable locations along a surface 15 of tube 11.

In the presently preferred embodiment, tube 11 is operative to generate an electron beam 17 that is deflectable within the tube 11 to impact at various points along the target 19, which is within tube 11 opposite outer surface 15. Electron beam 17 may be deflected to traverse various patterns, such as beam raster pattern 21. It is to be understood, however, that beam 17 may alternatively be deflected to traverse other patterns such as a circular or rectangular pattern, instead of the raster pattern 21.

As a consequence of electron beam 17 striking target 19, X-rays are emitted from outer surface 15 of X-ray tube 11 in accordance with conventional radiographic principles well understood by those in the art. At each point that the electron beam 17 traverses along raster pattern 21, a fan like pattern of X-rays 23 is emitted from the corresponding point on opposing surface 15. As illustrated at FIG. 1, at Time $T_0$ electron beam 17 is directed to point 25, resulting in a fan-like pattern of beams 23 eminating from the corresponding point on the opposite surface of tube 11.

Detector array matrix 13 is preferably formed of a plurality of detector array elements 27 innerconnected to form a planner surface disposed generally opposite surface 15 of tube 11. Though the detector array matrix 13 is preferably disposed substantially parallel to surface 15 of tube 11, the present invention does not require array 13 to be situated in any particular angular relation to the tube 11. It is also anticipated that the relationship between the point source and the selected detector element may be dynamically varied in accordance with a predetermined function. As described more fully below in connection with FIGS. 4 and 5, various methods and apparatus for sampling the outputs of a predetermined pattern of detector array elements may be effected utilizing components and processing techniques well known to those of ordinary skill in the art.

As shown at FIG. 1, the rays 23 eminating from point 25 on tube 11 impact the surface of detector array matrix 13 at various angles. Rays 23 include rays 29 that impact the surface of detector array matrix 13 at an oblique angle, and ray 31 that impacts normal to the surface of detector array matrix 13. Though each of the array elements 27 are individually excitable by the incident X-rays, the present invention is operative to selectively sample outputs from the detector elements, e.g., only those elements excited by incident X-ray beams striking the detector elements 27 at a desired angle of incidence i.e., with the respect to the plane of the dector surface. The invention thus selects outputs only from those detector array elements in a predetermined position with respect to the contemporaneous location of the point source 25 of the X-ray beams. Though the distance between tube 11 and array matrix 13 is variable and need not be limited to any particular range, it is anticipated that in many practical applications the tube 11 may be disposed close to the surface of array matrix 13, e.g., approximately three to eight inches (3"-8").

FIG. 2 illustrates the same structure disclosed at FIG. 1, except that the point source is disposed at a different position 26 along the surface of tube 11. As was the case with FIG. 1, a fan of X-ray beams eminates from point 26 and strikes the surface of the detector array matrix 13 at various angles. Though each detector element 27 upon which an X-ray beam is incident may be excitable by that beam, the outputs of only a selected one or more of the detector elements is contemporaneously output for processing and/or display. The relationship between the point source and the selected element remains the same, e.g., only the element directly opposite the point source 26 is sampled as the point source traverses the surface of tube 11.

The selected relationship between the detector element whose output is sampled and the location of the point source along the opposing surface of tube 11, may be selected in accordance with the particular application or the physical characteristics of the object being imaged. That spatial relationship may be varied to permit viewing of the object to be X-rayed from various angles of incidence. Views from different angles of incidence may provide greater detail of the three dimensional object being examined. Moreover, the selective time varient interrogation of detector array elements in conjunction with the instantaneous position of the source of the x-ray beam avoids contemporary problems associated with the appearance of shadows on the image. Such shaddows result from the combined effects of overlapping x-ray beams having differing angles of incidence, yet impacting the detector surface at the same location, i.e., X-ray beams that were transmitted from different positions and pass through the object at different angles.

Figure 3:
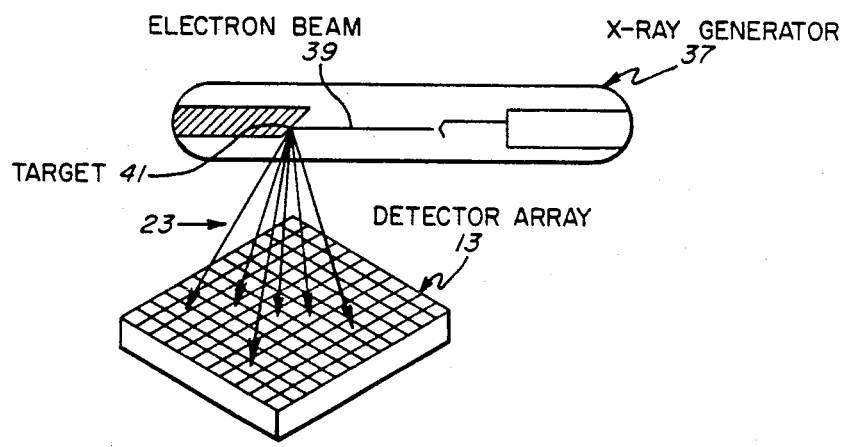

FIG. 3 illustrates an alternative embodiment of the present invention utilizing a different X-ray generator. Though the alternative X-ray generator 37 functions to transmit a pattern of X-ray beams in a different manner than tube 11, illustrated at FIGS. 1 and 2, the location and direction of the X-rays emitted from the X-ray generator 37 may also be varied, and the sampled detector element output may be selected in accordance with such location and direction variations, in substantially the same manner as described in connection with FIGS. 1 and 2.

Figure 4:
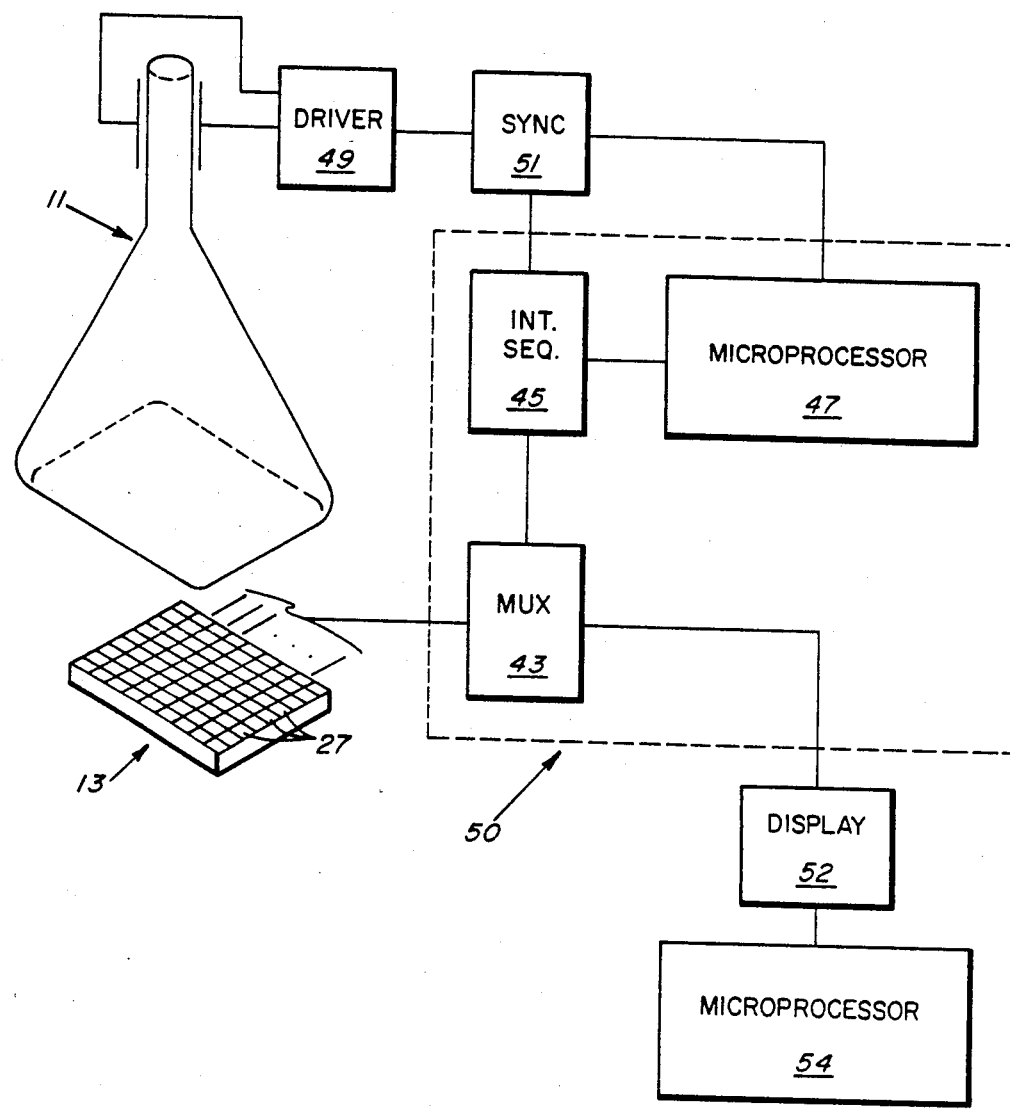
FIG. 4 is a circuit diagram illustrating exemplary synchronization and output control circuitry.

FIG. 4 illustrates an exemplary circuit diagram that may be used to effect selective sampling of the detector array matrix 13 in conjunction with the movement of the X-ray point source. As previously indicated, detector array 13 is preferably formed of a planner array of detector elements 27. Each of the elements 27 is separately exciteable so as to produce an output signal when an X-ray beam is incident upon that element. The output of each element 27 may be separately coupled to a multiplexer 43 within output control circuit 50. Multiplexer 43 may be any of various commercially available devices such as the model 7100 Multiplexer produced by ITI Switching Inc. Multiplexer 40 operative to selectively communicate the output of one or more detector elements 27 to a display 52 in accordance with control signals received from interrogator sequencer 45. Microprocessor 47 is operative to regulate the sequencing function of interrogator sequencer 45 such that sequencer 45 enables the appropriate output signals from multiplexer 43 at the correct time.

Synchronization circuit 51 is in electrical communication with X-ray tube driver 49 and interrogator sequencer 45, which controls the particular detector element 27 being interrogated at a particular time. Synchronization circuit 51 provides clock signals to driver 49 and sequencer 45 so as to synchronize the instantaneous movement of the X-ray source along the surface of tube 11, and the interrogation of the detector elements 45. Synchronization circuit 51 is preferably responsive to control signals from microprocessor 47, in output control circuit 50, which also communicates control signals to interrogator sequencer 45. Those control signals from microprocessor 47 effectively permit variations of the relationship between the location of the X-ray source and the contemporaneous location of the sampled detector elements.

In one application, synchronization circuit 51 and output control circuit 50 cooperate such that only the detector element directly opposite the point source is sampled as the X-ray source traverses a pattern along the surface of tube 11. In such a scenario the detector array may effectively respond only to X-rays having an angle of incidence substantially normal to the upper surface of the detector elements. Alternatively, synchronization circuit 51 and output control circuit 50 can cooperate to adjust the sampling of the detector array such that only detector elements laterally offset from the contemporaneous location of the point source are interrogated. In that scenario the circuitry is effective to limit the response of the detector matrix only to X-rays having an angle of incidence oblique to the upper surface portion of the detector. Consequently, the precise angle of X-ray imagery of the object under investigation may be varied under the control of microprocessor 47, i.e., the relative positions between the instantaneous location of the point source and the location of the sampled detector element(s) may be selectively varied.

Microprocessor 54 is connected to display 52 and is adapted to map images of the object under examination from various angles. Microprocessor 54 will then communicate signals back to display 52 in order to illustrate a composite representation of the object being examined, showing features of the object in three dimensions.

By the foregoing technique, it should be apparent to those of ordinary skill in the art that the present invention is effective to selectively focus an X-ray image at any of a wide range of angles of incidence. Thus, objects having irregular shapes and surfaces may be imaged from various angles without degradation of image quality due to overlapping X-ray beams.

In field use, it may be difficult to determine whether the array 13 is disposed substantially parallel to and opposite the lower surface of tube 11. Accordingly, it may be difficult to determine the desired synchronization based solely upon the supposed relative positions of the tube 11 and array 13. However, visual inspection of display 52, in conjunction with variation of synchronization circuit 51 permits dynamic modification of the synchronization relationship between the movement of the X-ray point source and the sampling of the detector elements 27 in order to arrive at the clearest synchronization setting for the surface area that the operator desires to view.

Though one exemplary synchronization and sampling circuit is illustrated at FIG. 4, it will be recognized by those of ordinary skill in the art that various other equivalent sampling and synchronization circuits may be utilized without departing from the spirit and scope of the present invention. Moreover, it will also be recognized that although the above description is principally directed to variable selective interrogation of the detector array element in relation to a fixed pattern of movement of the X-ray source, it is recognized that, in an alternative embodiment, the detector sampling pattern may remain constant and the contemporaneous location and/or activation of the X-ray source may be varied. In either case, i.e., selective variation of the detector sampling pattern or selective variation of the X-ray point source, the significant consequence is that the contemporaneous spacial relationship between the point source and the sampled detector element is made selectively variable so as to limit X-ray imagery to a desired angle of incidence.

Figure 5:
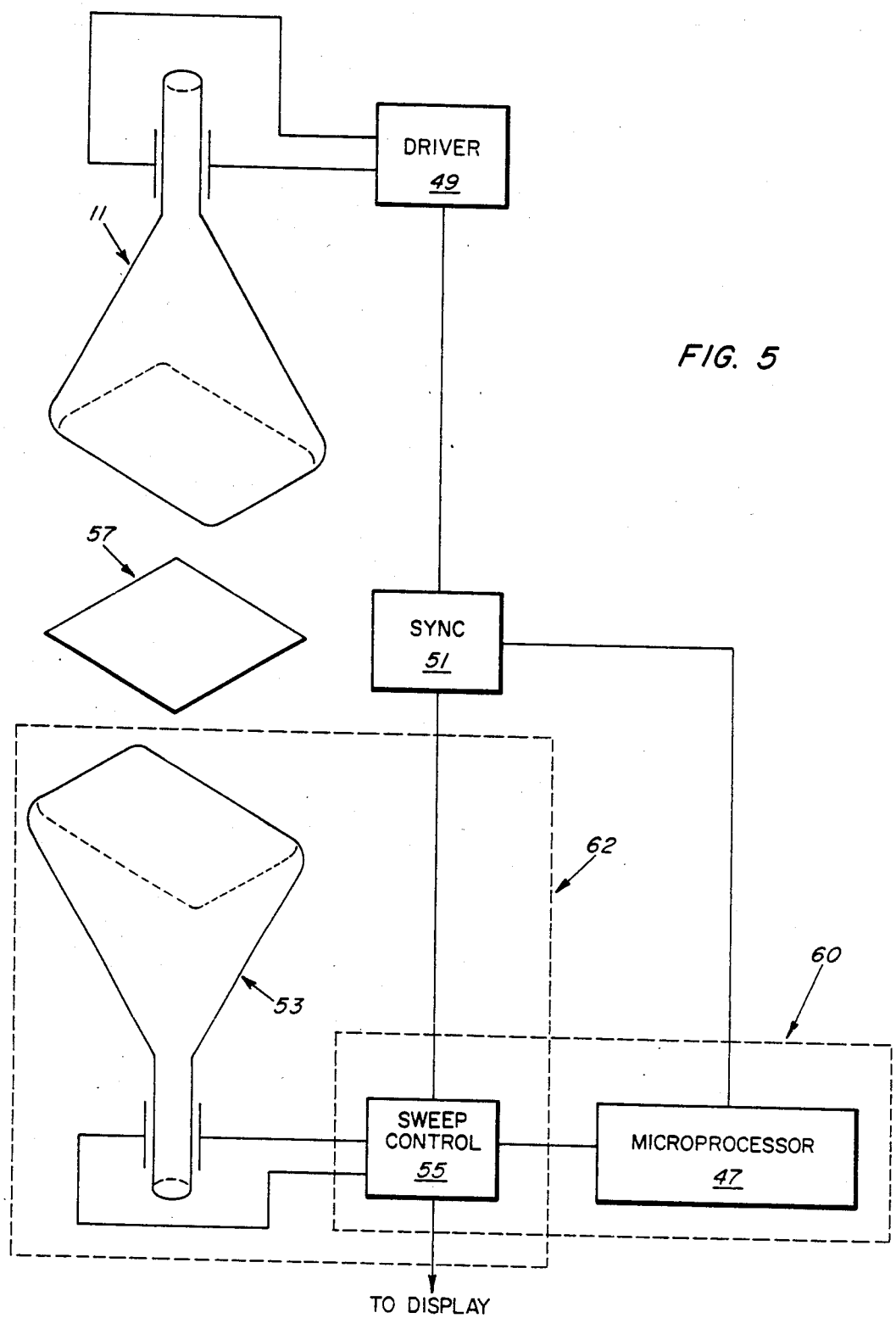
FIG. 5 is a perspective view illustrating the use of an alternative X-ray generator.

FIG. 5 illustrates an alternative embodiment of the present invention wherein the detector array matrix 13 is replaced by screen 57 and a television camera 62 comprising detection tube 53, and sweep control 55. In the embodiment illustrated at FIG. 5 transducer screen 57 is operative to translate incident X-ray beams into light signals at points corresponding with the location at which the incident X-ray beam strikes the surface of screen 57. Camera tube 53 and sweep control 55 are operative to perform a raster scan the surface of camera tube 53 opposite screen 57 to generate electrical output signals representative of the instantaneous location of light signals incident on the surface of camera tube 53.

Synchronization circuit 51 provides clock signals to sweep control 55 and x-ray tube driver 49, which collectively control the instantaneous movement of the scan point along the surface of camera tube 53 and the contemporaneous location of the X-ray point source along the lower surface of X-ray tube 11, respectively. As discussed in connection with FIG. 4, synchronization circuit 51 is preferably responsive to control signals from microprocessor 47 in output control circuit 60. Microprocessor 47 is adapted to generate a control signal to synchronization circuit 51 in order to vary the timing of the scan of the surface of camera tube 53 in relation to the movement of the point source of the surface of X-ray tube 11. Thus, the spacial relationship between the scan point(s) and the location of the x-ray point source may be varied through a wide range of relative positions such that, as with the circuit described at FIG. 4, the object to be imaged may be viewed from any of a variety of angles of incidence.

As was also described in connection with Figure 4, the circuitry illustrated in FIG. 5 may be varied such that the scan of the camera tube 53 remains constant and the activation and/or contemporary location of the X-ray point source within tube 11 may be varied to effect the desired spacial relationship between the location of the point source and the scan point.

In the presently preferred embodiment, X-ray tube 11 may be based on any of a variety of commercially available cathode ray tubes such as those manufactured by EMI/THORENS of New Jersey, with an operating voltage increased to a minimum of approximately 50 kv. The higher voltage level provides sufficient energy so as to measure the emission of photons as the electron beam strikes the target. It is also preferred that a normal phosphorous interior coating be replaced with a coating of alternative material, such as tungsten, which is more effective in translating the impacted electron beam into X-rays. A 0.002 ∝ to 0.003" layer of tungsten is presently believed to be sufficient to facilitate operation of the invention. Alternative types of cathode Ray tubes that irradiate a point on the face of the tube from the front of the tube, rather than from the rear, e.g. Sinclair tubes may also be used in conjunction with the present invention.

Detector array matrix 13 may be any of a number of rays of detector elements, such as the CCD222 detector, manufactured by Fairchild Corporation.

Transducer screen 57 may be any of a number of commercially available screens adapted to translate incident X-rays into light signals, such as the image intensifying screen manufactured by Hamamatsu Corporation. Another exemplary device suitable for use in connection with the present invention is an intensifier tube adapted to form a visable image of an object irradiated by X-rays. Such advice, described in connection with associated circuitry, is disclosed in U.S. Pat. No. 4,543,605 for "X-ray Examination Apparatus." The television camera, including camera tube 53 and sweep control 55 may be any of a number of commercially available television cameras such as the Vidicon camera manufactured by RCA. Microprocessors 47 and 54 may be commercially available devices such as the model PCXT microprocessor produced by IBM.

Though the present invention has been described in connection with the presently preferred embodiment, it is anticipated that various modifications and additions may be made to that embodiment without departing from the spirit and scope of the present invention, which is defined by the appended claims.

What is claimed is:

1. An x-ray imaging device for selective imaging of an object comprising:
   an X-ray source having means to variably dispose a point source of X-rays about a first surface of the X-ray source:
   a detector spaced from said X-ray source opposite the object to be imaged, said X-rays being incident upon a surface of said detector; and
   an output control circuit connected to said detector and said X-ray source, said output control circuit having means to selectively enable an output from said detector based upon the value of incidence of said X-rays upon said detector surface so that said detector output is enabled only when the X-rays strike the detector surface at a desired angle of incidence, said output control circuit including circuitry for varying said desired angle of incidence.

2. The device as recited in claim 1 wherein said output control circuit has means to enable said detector to respond only to X-rays having a selective angle of incidence relative to a first surface portion of said X-ray source.

3. The device as recited in claim 1 wherein said output control circuit has means to enable said detector to respond only to X-rays having an angle of incidence substantially normal to a first surface portion of said detector.

4. The device as recited in claim 1 wherein said detector has means to respond only to X-rays having an angle of incidence oblique to a first surface portion of said detector.

5. The device as recited in claim 1 wherein said detector has means to translate said X-rays into electrical signals.

6. The device as recited in claim 1 wherein said detector comprises a plurality of discrete detector elements.

7. An X-ray imaging device for selective imaging of an object comprising:
   an X-ray source having means to variably dispose a point source of X-rays about a first surface of the X-ray source;
   an array of detector elements spaced from said X-ray source opposite the object to be imaged, said X-rays being incident upon said array, said detector elements, having means to translate said X-rays into electrical signals; and
   a detector interrogator sequencer, said sequencer having means to selectively interrogate the output of individual detector element based upon the value of the angle of incidence of said x-rays upon said individual detector 8. The device as recited in claim 7 wherein said sequencer has means to interrogate only detector elements that are positioned substantially normal to the instantaneous position of said point source.

9. The device as recited in claim 7 wherein said sequencer has means to interrogate only detector elements that are positioned at an acute angle in relation to the instantaneous position of said point source.

10. The device as recited in claim 7 wherein said sequencer has means to selectively interrogate detector elements disposed at a predetermined position relative to the instantaneous position of said point source.

11. An X-ray imaging system comprising:
    an X-ray tube herein means to emit a fan pattern of X-rays from a point source, said X-ray tube including a target and a glass housing, said point source being movably disposed along a first surface of said glass housing,
    a plurality of detector elements disposed in space opposed relation to said housing first surface said fan pattern of X-rays being incident upon a first surface of said detector elements, said
    detector elements having means to generate an output signal in response to incident X-rays; and detector output control circuitry having means to selectively sample the output of an individual detector element based upon the value of the angle of incidence of said x-rays upon said individual detector element so that outputs of individual detector elements are sampled only when the individual elements are in a desired spacial relationship with said point source, said output control circuitry including circuitry for varying said desired spacial relationship.

12. The system as recited in claim 11 wherein said detector output control circuitry has means to sample only the outputs of detector elements having a first surface disposed at a substantially normal angle in relation to the location of said point source.

13. The system as recited in claim 11 wherein said detector output control circuitry has means sample only the outputs of detector elements having a first surface disposed at an oblique angle in relation to the location of said point source.

14. The system as recited in claim 11 further including a detector synchronization circuit connected to said detector output control circuitry and having means synchronize sampling of said detector elements to movement of said point source such that the spatial relationship between the sampled detector element and the location of the point source remains substantially constant as said point source moves and different detector elements are progressively sampled.

15. The system as recited in claim 14 wherein said synchronization circuit includes a variable synchronization control having means to vary the synchronization between said point source and the sampled detector element such that the spatial relationship between the point source and the sampled detector element may be selectively varied.

16. The system as recited in claim 11 wherein said detector elements comprise a planar array of individually excitable detector elements.

17. The system as recited in claim 11 wherein said detector elements comprises a television camera detection tube having means to translate light signals into electrical signals, and an (X-ray transducer connected to said camera and having means to translate said incident X-rays into light signals.

18. The system as recited in claim 17 wherein said detector output control circuitry comprises a television camera sweep control circuit, said sweep control circuit having means to perform a raster scan of the said detector elements.

19. The system as recited in claim 18 further comprising a camera synchronization circuit connected to said sweep control circuit and having means to synchronize said raster scan to movement of said point source, such that the relationship between the location of the point source and the raster scan remains substantially constant.

20. The system as recited in claim 19, further including a microprocessor operatively connected to said camera synchronization circuit and said sweep control circuit, said microprocessor having means to selectively vary the relationship between the movement of the point source and said raster scan.

21. The device as recited in claim 11 further including three dimensional imaging circuitry has means to receive signals from said detectors elements and process said received signals to generate an image representative of a three dimensional view of said object.

22. The method of providing selective X-ray imagery of an object comprising:
generating a substantially fan like pattern of X-ray beams from an X-ray source;
varying the location of said X-ray source;
passing said X-ray beams through an object to be X-rayed;
receiving said X-ray beams upon the surface of a detector space from said X-ray source;
selectively responding to said X-ray beams in accordance with the angle of incidence of said X-ray beams upon the surface of said detector so that the output of said detector in enabled only when the X-ray strikes said detector surface at a desired angle of incidence; and
selectively varying said desired angle of incidence to facilitate X-ray imagery of the object.

23. The process as recited in claim 22 wherein the step of selectively responding to said X-ray beams comprises selectively responding to X-ray beams having an angle of incidence substantially normal to the surface of said detector.

24. The process as recited in claim 22 wherein the step of selectively responding to said X-ray beams comprises selectively responding to X-ray beams having an angle of incidence oblique to the surface of said detector.

25. The method as recited in claim 22 wherein said step of receiving said X-ray beams on the surface of a detector comprises receiving said X-ray beams on the surface of a detector array formed of individually excitable detector elements.

26. The process as recited in claim 25 further comprising the step of selectively interrogating the outputs of individual detector elements in accordance with the angle of incidence of said X-ray beams upon the surface of said detector elements.

27. The process as recited in claim 26 further including the step of synchronizing said interrogation of the detector elements with the movement of said point source such that the spatial relationship between the interrogated detector element and the location of the point source remain substantially constant as the point source moves and different detector elements are progressively interrogated.

28. A process for X-ray imagery of an object comprising:
generating a substantially fan-like pattern of X-ray beams from an X-ray source;
varying the location of the X-ray source;
passing the X-ray beams through an object to be imaged;
receiving the X-ray beams on the surface of a screen having means to translate incident X-ray beams into light signals;
scanning the surface of the screen so as to translate said light signals into electrical signals;
synchronizing said scan such that the value of an angle between the portion of the screen being scanned and the contemporaneous location of the point source remains substantially constant as the point source moves and different portions of the screen are sampled; and
varying the synchronization so that the spacial relationship between the portion of the screen being scanned and the contemporaneous location of the point source is varied between a plurality of spacial relationships to facilitate imagery of surfaces of the object.

* * * * *

UNITED STATES PATENT AND TRADEMARK OFFICE
CERTIFICATE OF CORRECTION

PATENT NO. : 4,718,075
DATED : January 5, 1988
INVENTOR(S) : Michael Horn

It is certified that error appears in the above-identified patent and that said Letters Patent is hereby corrected as shown below:

Column 1, line 23 change "penerate" to --penetrate--
Column 2, line 58 change "trnsducer" to --transducer--
Column 3, line 10 change "FIG. 5" to --FIG. 3--
Column 4, line 6 delete "the"
Column 7, line 10 change ".002 α " to --.002"--
Column 7, line 12 change "Ray" to --ray--
Column 7, line 54 change "value of incidence" to --value of the angle of incidence--
Column 8, line 26 change "detector" to --detector.--
Column 8, line 40 change "herein" to --having--
Column 8, line 44 change "housing," to --housing;--
Column 8, line 46 change "surface" to --surface,--
Colum 8, line 50 change "X-rays; and detector" to -- X-rays; and detector --

Column 8, line 67 change "has means sample" to --has means to sample--
Column 9, line 6 change "having means synchronize" to --having means to synchronize--
Column 9, line 26 change "and an (X-ray" to --and an X-ray--

Signed and Sealed this

Twentieth Day of December, 1988

Attest:

DONALD J. QUIGG

Attesting Officer

Commissioner of Patents and Trademarks